(12) United States Patent
Camus et al.

(10) Patent No.: US 8,275,448 B2
(45) Date of Patent: Sep. 25, 2012

(54) METHOD FOR RECONSTRUCTING A 3D PRESENTATION

(75) Inventors: Estelle Camus, Erlangen (DE); Thomas Redel, Poxdorf (DE)

(73) Assignee: Siemens Aktiengesellschaft, München (DE)

( * ) Notice: Subject to any disclaimer, the term of this patent is extended or adjusted under 35 U.S.C. 154(b) by 1601 days.

(21) Appl. No.: 11/715,533

(22) Filed: Mar. 8, 2007

(65) Prior Publication Data

US 2007/0232886 A1 Oct. 4, 2007

(30) Foreign Application Priority Data

Mar. 10, 2006 (DE) .................. 10 2006 011 242

(51) Int. Cl.
*A61B 5/05* (2006.01)
(52) U.S. Cl. ..................................... 600/428
(58) Field of Classification Search ............... 600/428
See application file for complete search history.

(56) References Cited

U.S. PATENT DOCUMENTS

| 5,724,978 | A | 3/1998 | Tenhoff |
| 6,148,095 | A | 11/2000 | Prause et al. |
| 2002/0049375 | A1 | 4/2002 | Strommer et al. |
| 2006/0036167 | A1 | 2/2006 | Shina |

FOREIGN PATENT DOCUMENTS

| DE | 103 38 690 A1 | 12/2004 |
| WO | WO 97/28743 A1 | 8/1997 |
| WO | WO 2004/032740 A2 | 4/2004 |

OTHER PUBLICATIONS

Bárbara Martín-Leung, Kai Eck, Jörg Bredno, Til Aach; "X-IVUS: Integrated x-ray and IVUS system for the Cathlab"; Medical Imaging 2005; pp. 378-387; Proc. of SPIE; vol. 5744; Bellingham, WA, USA.
Sebastiaan A. De Winter, Ronald Hamers, Muzzafer Degertekin, Kengo Tanabe, Pedro A. Lemos, Patrick W. Serruys, Jos R.T.C. Roelandt, Nico Bruining, "Retrospective Image-Based Gating of Intracoronary Ultrasound Images for Improved Quantative Analysis: The Intelligate Method", Catheterization and Cardiovascular Interventions, Jan. 2004, pp. 84-94, vol. 61, Wiley-Liss, Inc.
Cornelis J. Slager, Jolanda J. Wentzel, Johan C.H. Schuurbiers, Jan A.F. Oomen, Jeroen Kloet, Rob Krams, Clemens Von Birgelen, Willem J. Van Der Giessen, Patrick W. Serruys, Pim J. De Feyter, "True 3-Dimensional Reconstruction of Coronary Arteries in Patients by Fusion of Angiography and IVUS (ANGUS) and its Quantitative Validation", Circulation, Aug. 1, 2000, pp. 511-516.

*Primary Examiner* — Brian Casler
*Assistant Examiner* — Saurel J Selkin

(57) ABSTRACT

The invention relates to a method for reconstructing a 3D presentation of a hollow organ based on two-dimensional catheter images, comprising: detecting at least two fluoroscopy images at two different angles of the hollow organ; determining a start position of the catheter from the fluoroscopy images in a three-dimensional model of the hollow organ or a catheter guide; determining a probable withdrawal path of the catheter based on the three-dimensional model; withdrawing the catheter while recording the catheter images and assigning a withdrawal length to each catheter image; determining the deviation of the position of the catheter from a central path running through the middle of the hollow organ and the orientation of the catheter for each catheter image based on the withdrawal path and the withdrawal length; and reconstructing the 3D presentation from the two-dimensional catheter images as well as the deviation of the position of the catheter.

18 Claims, 3 Drawing Sheets

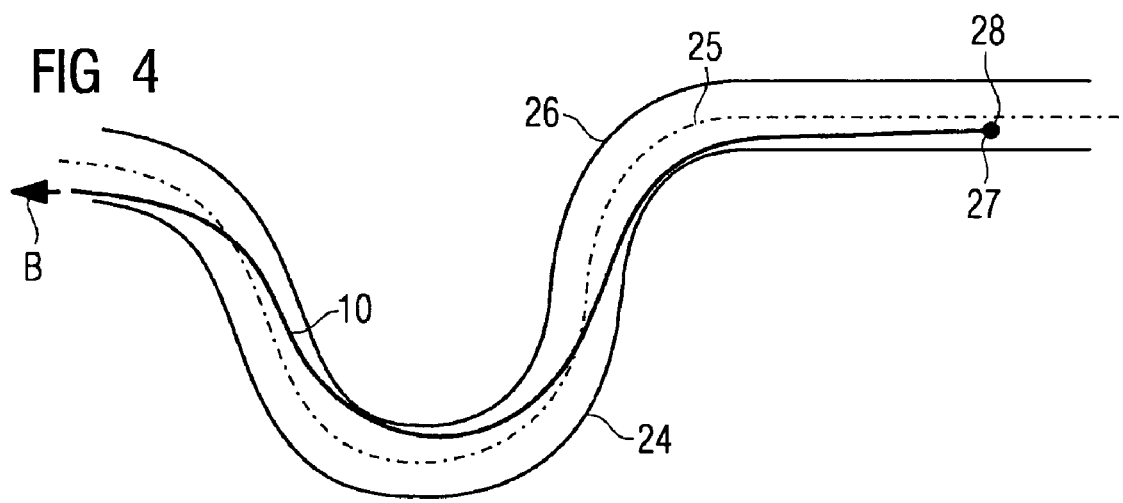
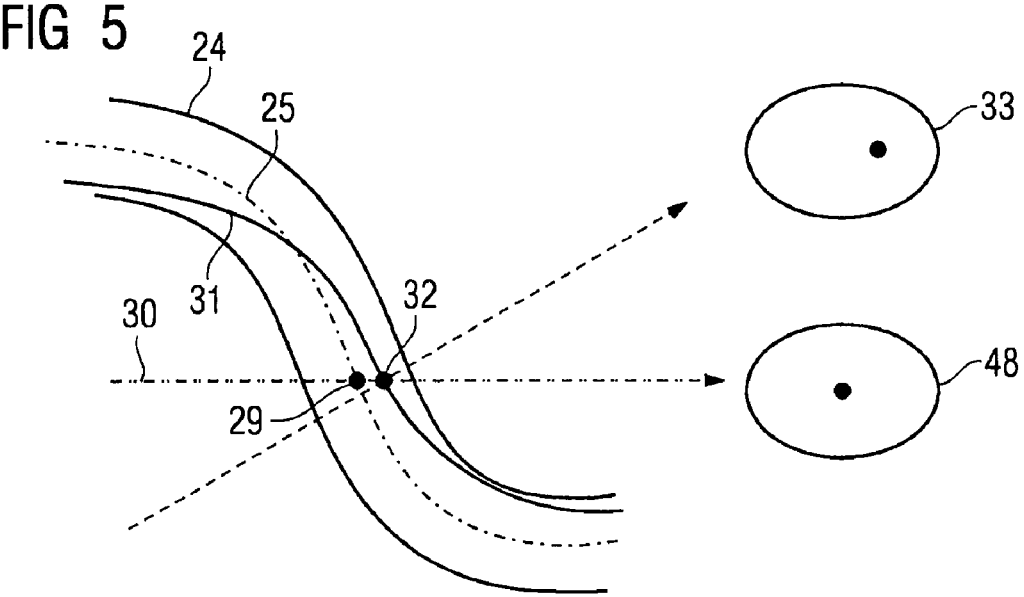

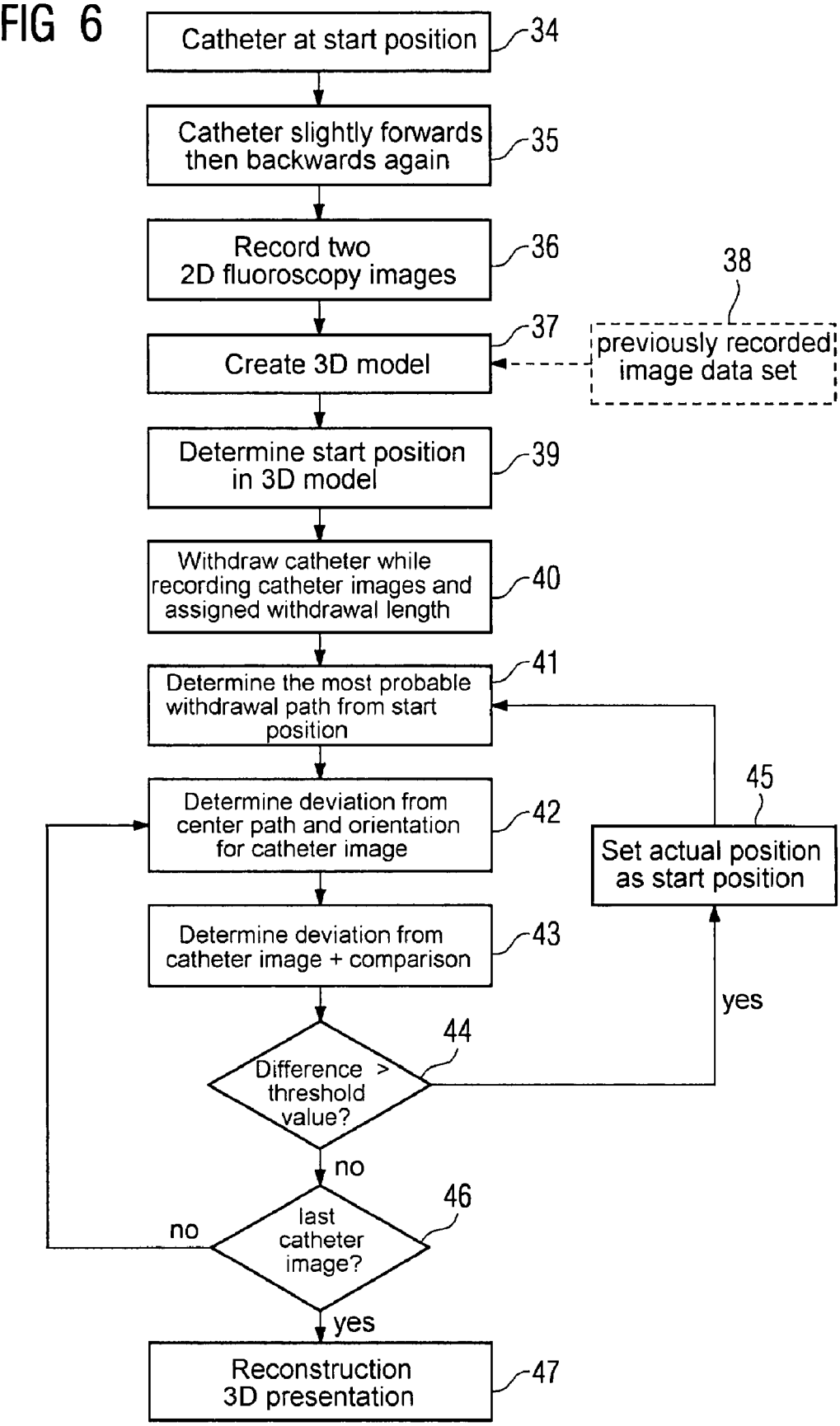

METHOD FOR RECONSTRUCTING A 3D PRESENTATION

CROSS REFERENCE TO RELATED APPLICATIONS

This application claims priority of German application No. 10 2006 011 242.3 filed Mar. 10, 2006, which is incorporated by reference herein in its entirety

FIELD OF THE INVENTION

The invention relates to a method for reconstructing a 3D presentation of a hollow organ on the basis of two-dimensional catheter images recorded during its withdrawal by a catheter comprising an image recording device.

BACKGROUND OF THE INVENTION

For diagnosis and therapy planning in medical fields relating to hollow organs, especially in interventional cardiology, the process of obtaining information about the hollow organ from x-ray based imaging methods is known. These methods at best however only deliver information about the lumen, not about the wall structure of the vessel. Invasively applied imaging catheters, which include an imaging device, provide information about the wall structure. These imaging devices are based for example on ultrasound imaging (IVUS) or OCT (optical coherence tomography). In such cases mostly two-dimensional sectional images are obtained, with a 3D reconstruction of these two-dimensional catheter images not being possible a priori because of the unknown position and orientation in the hollow organ at the moment when the image is recorded. Different technical solutions have thus been proposed to allow the reconstruction of a 3D presentation of the hollow organ, especially of the vessel, to still be obtained.

In a method for fusion of angiography and IVUS (ANGUS) it is proposed that the withdrawal of an WUS catheter be recorded using a biplane x-ray system from two different directions. The position and orientation of the IVUS catheter at any given point in time can be determined from the two fluoroscopy images at an angle to each other obtained in this way. The continuous recording of fluoroscopy images leads in this case however to an extreme radiation load for the patient.

Alternatively the use of a location system has been proposed, cf. US 2002/0049375 A1, with a sensor or such like being mounted at the tip of the catheter of which the position and orientation is recorded by a location system positioned outside the body. The disadvantage of this method is that additional devices and special catheters are needed.

A further method for reconstruction of a 3D presentation of a blood vessel is proposed in an article by B. Martin-Leung, K. Eck, J. Bred no and T. Each, "X-IVUS: Integrated x-ray and IVUS system for the Cathay", Medical Imaging 2005, Proc. of SPIE Vol. 5744, April 2005, pages 378 to 387. In this article two-dimensional WUS catheter images which belong to the same ECG phase of the heart cycle are sought out and a registration with previously recorded angiographic fluoroscopy images is undertaken. It is assumed here that the IVUS catheter tip is located in the center of the vessel lumen and moves at all times on this central line. However, two sources of error are then present:
a) On the one hand the catheter diameter is usually far smaller than the vessel diameter, i.e. the catheter will generally not be located in the center of the vessel lumen. This produces different effective withdrawal lengths, and in addition the alignment of the catheter can change during the withdrawal.
b) Another problem is that the orientation of the IVUS image plane relative to the vessel is unknown with this method. This means that distortions can arise for example during the reconstruction.

The article by Martin-Leung et al. does not disclose any reconstruction of a 3D presentation from the recorded IVUS catheter images, such a reconstruction would not be exact because of the sources of error identified under points a) and b) above.

SUMMARY OF THE INVENTION

The object of the invention is thus to specify a method which is designed to make possible a three-dimensional map of the structure of a hollow organ which is as correct as possible, including the wall structure, without the need for additional devices and without subjecting the patient to an increased radiation dose.

To achieve this object there is inventive provision, according to a method of the type stated above, for executing the following steps:
a) Recording at least two two-dimensional fluoroscopy images at an angle to each other showing the hollow organ and the catheter tip;
b) Determining a three-dimensional start position of the catheter from the fluoroscopy images in a three-dimensional model of the hollow organ or a catheter guide;
c) Determining a most probable withdrawal path of the catheter on the basis of the three-dimensional model;
d) Withdrawing the catheter while recording the catheter images while continuously detecting the withdrawal length, with each catheter image being assigned a detected withdrawal length;
e) Determining the deviation of the position of the catheter from a central path running through the middle of the hollow organ and the orientation of the catheter for each catheter image on the basis of the withdrawal path determined and the withdrawal length; and
f) Reconstruction of a 3D presentation of the hollow organ from the two-dimensional catheter images, taking into account the deviation of the position of the catheter from the central path and the orientation of the catheter.

In this case steps b) to d) can also occur in the order b), d), c) or d), b), c).

Thus, with the inventive method, after the catheter has been brought into its start position, two fluoroscopy images showing the hollow organ and the catheter tip are initially recorded at an angle to one another. From the fluoroscopy images showing the catheter from two different projections, a three-dimensional position can be determined according to generally known methods. The underlying idea of the present invention is now, with the aid of a three-dimensional model of the hollow organ or a catheter guide located in the hollow organ, to determine a possible withdrawal path of the catheter. In this case the withdrawal path is determined which naturally reflects the most probable withdrawal path. For the withdrawal path determined, the position of the catheter, more precisely that of the image recording device, as well as its orientation in the lumen of the hollow organ are known for each withdrawal length. Since the withdrawal path has been determined so that it is most likely to reflect the real withdrawal path, each catheter image to which a withdrawal length is assigned can now be assigned a deviation of the position of the image recording device of the catheter from a central path running through the middle of the hollow organ and the orientation of the catheter, more precisely that of the image recording device. Finally this makes it possible to reconstruct a 3D presentation of the hollow organ which is as correct as possible, since the errors arising through the deviation of the catheter from the central path and the non-ideal orientation of the catheter images can be corrected.

Since in most cases the catheter images recorded are sectional images, such sectional images are also to be used as a basis below, without any limitation being imposed by this approach. It is naturally equally easily possible to record the surface of the wall of the hollow organ with a suitable image recording device and to reconstruct a 3D presentation of the hollow organ from this.

The inventive solution advantageously needs no additional hardware outlay, such as a positioning system for example, since the most probable withdrawal path is determined in a three-dimensional model. In addition no ongoing x-ray monitoring is necessary so that the patient is not exposed to too high a radiation dose. Information about the hollow organ or the behavior of the catheter, especially of the image recording device, existing in any event is used advantageously in the inventive method to predict the withdrawal path.

It should be noted at this point that the determination of the possible withdrawal path does not have to be undertaken before the withdrawal of the catheter and the recording of the catheter images, but can also be performed afterwards.

To obtain the 3D model of the hollow organ or the catheter guide, two primary alternatives are possible in accordance with the invention. On the one hand the three-dimensional model can be created on the basis of the fluoroscopy images. In this case the fluoroscopy images recorded in any event are advantageously also used for creating the three-dimensional model. No further images need then be recorded.

In a further embodiment provision can be made here for a sleeve catheter with a sleeve forming the catheter guide to be used as the catheter, in which the image recording device is withdrawn within the fixed sleeve. As regards the creation of the three-dimensional model there are three different cases to be considered here. In one case the sleeve can be seen in the fluoroscopy images. If the sleeve is transparent in the fluoroscopy images, i.e. it cannot be seen, the catheter guided in the sleeve can be visible. In these two cases there can be provision for the three-dimensional model of the catheter guide to be created in the fluoroscopy images on the basis of the representation of the sleeve or of the catheter guided in the transparent sleeve. A sleeve catheter thus comprises a sleeve visible in the fluoroscopy images which is transparent for the image recording device, or in the case of a transparent sleeve, a catheter visible in the fluoroscopy images. The image recording device is withdrawn within the sleeve while the sleeve remains in place in the hollow organ. In order to obtain the three-dimensional model, the passage of the sleeve or of the catheter is extracted from the fluoroscopy images by means of an image processing system for example. The withdrawal path is then extrapolated and determined from the known passage of the withdrawal path within the sleeve. The use of such a sleeve catheter also allows an especially simple determination of the withdrawal path.

It is however also possible for both the sleeve and also the catheter to be transparent for the fluoroscopy images, i.e. not be visible within them. Then only the catheter tip is able to be localized. In this case the three-dimensional model of the hollow organ is created from the fluoroscopy images and simulated as described below.

The three-dimensional model can also be a model of the hollow organ and be obtained from the presentation of the hollow organ on the fluoroscopy images. The hollow organ can also be seen from two projections in the fluoroscopy images at an angle to each other, so that its lumen can be reconstructed as a three-dimensional model.

As an alternative to determining the three-dimensional model solely from the fluoroscopy images there can be provision for the three-dimensional model of the hollow organ to be created on the basis of an earlier image data set recorded, and for the start position in the three-dimensional model to be determined by registration of the fluoroscopy images with the 3D image data set. Frequently previously recorded image data sets from other imaging modalities are already present. These can for example be image data sets of magnetic resonance and/or computer tomography images. In this case there are different methods to determine the passage of a hollow organ in three dimensions, and also the extent of its lumen. Using the fluoroscopy images showing the same area, the coordinate systems of the previously recorded data set and those of the fluoroscopy images can now be registered with each other. Since however the start position of the catheter in the coordinate system of the fluoroscopy images can be determined, it is then consequently also known in the three-dimensional model which was created on the basis of the image data set created previously. Already known, previously recorded and more exact information about the corresponding hollow organ is advantageously used in this variant.

In a further embodiment of the invention the following steps can be executed for determining the most probable withdrawal path:

Positioning a virtual catheter at the start position in the three-dimensional model, Determining of the most probable withdrawal path from a simulation of the virtual catheter in the three-dimensional model.

A simulation is also performed in accordance with the invention which is able to predict the behavior of the catheter on withdrawal and from this is able to determine the most probable withdrawal path. In this case, as well as the geometry known from the three-dimensional model, certain physical basic facts for movement of a body in the form of parameters and/or interrelationships are known. Expediently at least one physical parameter of the virtual or real catheter can be taken into consideration in the simulation. Such a physical parameter can for example be its diameter, specific weight, elasticity, rigidity and/or surface properties. Consequently knowledge about the physical characteristics of the catheter or the catheter tip are used in this variant, physical characteristics which under some circumstances can have a great influence on the behavior of the catheter. Thus the elasticity determines the way in which the catheter "lies" within an existing free space. The physical parameters can in this case be both measured in the real catheter or assumed, for example be average values for the virtual catheter. Similarly physical characteristics of the hollow organ or the catheter guide can also naturally be taken into account. Thus a model for hollow organ deformations arising can also be taken into consideration in the determination of the possible withdrawal path. Especially advantageously possible discontinuous movements of the catheter, especially a jump to another wall of the hollow organ and/or an onwards jump along the wall can also be taken into account in the simulation. Thus withdrawal paths can also be detected in which the tip of the catheter, for example through the resolution of a twist, in practice jumps from one wall to another. Likewise account can be taken of the fact that the catheter, for example with unevenness in the wall of the hollow organ, makes smaller jumps after catching on the wall.

The information about the deviation of the catheter from the central path can also be determined from the catheter images. The position of the catheter is relatively easy to establish within this, especially with sectional images. Preferably the deviation of the catheter from the central path during the reconstruction is also determined from the catheter images. In addition a fixed threshold value for the difference between the deviation from the central path determined from the most probable withdrawal path and the deviation from the central path determined from the catheter images can then be predetermined, which, if the most probable withdrawal path is exceeded, is recalculated as from the position at which the threshold was exceeded and is used for reconstruction of the newly calculated most probable withdrawal path. It is also proposed that ongoing checking be performed during the reconstruction on the basis of the deviation information able to be derived from the catheter images, to determine whether the withdrawal path determined is also the actual withdrawal path taken by the catheter. If a larger deviation occurs, the simulation can for example be executed again, with the known deviation and the assumed orientation of the catheter tip at the instantaneous position being taken as the start point. Should an error have consequently occurred in the determination of the most probable withdrawal path, this can be monitored and the probable withdrawal path can be iteratively adapted.

The ECG phase in the instantaneous heart cycle has a major role to play, especially in recording of blood vessels such as the coronary arteries for example. The movement of the heart to pump blood through the human body also, especially for the blood vessels in the vicinity of the heart, has effects on the form or extent of the hollow organ. The instantaneous ECG phase, with the ECG phase here being intended to describe a point in time or a time segment in the heart cycle, in which the geometry of the observed hollow organ only changes slightly or not at all, must in such cases be included without fail in the method for reconstruction of a 3D presentation. By and large two options are conceivable for this.

On the one hand there can be provision for the recordings to be triggered on the basis of a fixed ECG phase, with the ECG phase of the fluoroscopy images, the catheter images and where necessary of the model recorded earlier matching. In principle this creates an instantaneous image of the hollow organ at a specific ECG phase. ECG triggering is a well-known technique which will not be explained in any greater detail here.

As an alternative there can preferably be provision for the instantaneous ECG phase to be recorded for each detected catheter image and for images of the same ECG phase to be used in the reconstruction for a separate reconstruction in each case. If the ECG is accordingly continuously recorded and the respective ECG phase assigned to the images, many instantaneous recordings at different ECG phases can be created. Images in this case mean both the fluoroscopy images and the catheter images as well as if necessary the images of the previously recorded image data set. Naturally a reconstruction at a specific ECG phase can only be undertaken completely if fluoroscopy images are present for each ECG phase. Thus provision can be made especially advantageously for the fluoroscopy images to be recorded over at least one complete heart cycle and at least two fluoroscopy images of an ECG phase to be assigned in each case to the catheter images with the corresponding ECG for reconstruction. This allows instantaneous images to be recorded over the entire heart cycle. These can now be further processed in one of two ways. One involves the 3D reconstructions of the various ECG phases being fused together. This means that the effects occurring as a result of the heart cycle and the different heart phases can be computed retrospectively using an image processing system or a suitable algorithm back to the state at a specific ECG phase and the images can be combined into a single 3D reconstruction at this specific ECG phase. This means that data of the entire heart cycle can advantageously be used in a 3D presentation. Alternatively there can also be provision for the 3D reconstruction of the individual ECG phases to be combined into a time-resolved 4D reconstruction. This creates a kind of film which also clearly shows the change in the geometry and structure of the hollow organ during the heart cycle.

To allow the most reliable possible determination of the possible, most probable withdrawal path, it is sensible to have a fixed, known start configuration. In a further embodiment of the method it is thus advantageous for the catheter to be first advanced distally a short distance beyond the start position in order to then be withdrawn to the start position, and for the resulting shortest distance covered by the catheter to be taken into consideration for determination of the most probable withdrawal path. This adjustment of the catheter can for example be undertaken by the device which also handles the even withdrawal and the detection of the withdrawal length. If the catheter is withdrawn a little, it becomes slightly more rigid, to follow the shortest movement path. In other words this creates a permanently defined initial position.

Images derived from the catheter images can also be used for reconstruction of the 3D presentation. One example of this is what is known as ultrasound elastography. In this case a light pressure is exerted by the catheter tip on tissue of relevance for diagnosis during the usual ultrasound examination in the hollow organ. As a result small movements in consecutive ultrasound recordings are determined which produce the elastography image.

An IVUS device and/or an OCT device and/or an OFDI device can be provided as a suitable image recording device in the inventive method for example. All these modalities create sectional images which reproduce both the surface and also the tissue structure of the hollow organ.

It conclusion it should also be pointed out that the human breathing cycle can of course also have an effect on the hollow organ, for example the air tubes. Thus triggering based on the breathing phase can also be undertaken or the patient is asked to hold their breath while the images are being recorded for example.

BRIEF DESCRIPTION OF THE DRAWINGS

Further advantages and details of the invention emerge from the exemplary embodiment described below as well as with reference to the drawings. The figures show.

DETAILED DESCRIPTION OF THE INVENTION

Figure 1:
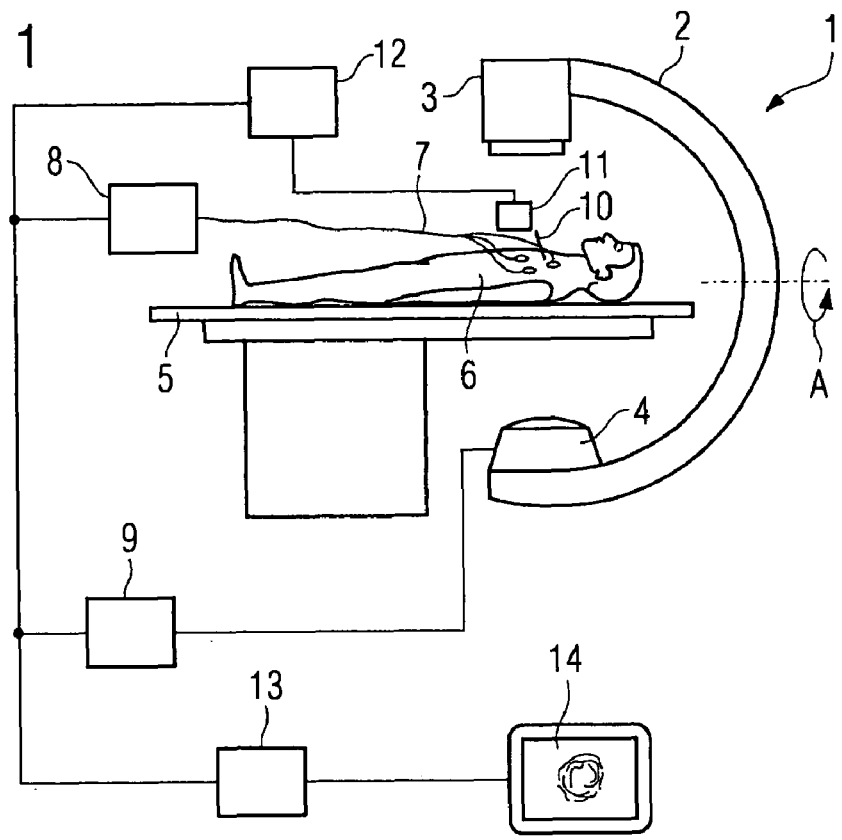
FIG. 1 the basic diagram of an examination apparatus embodied to execute the inventive method, FIG. 2 a catheter with an image recording device arranged at its tip, FIG. 3 a sleeve catheter with an inner catheter able to be moved within a sleeve forming the catheter guide, FIG. 4 a catheter within a hollow organ, FIG. 5 a basic diagram to explain the effects of different orientations, and FIG. 6 a flowchart of the inventive method.

FIG. 1 shows a medical examination device 1, suitable for executing the inventive method. A C-arm-x-ray system 2, comprising a radiographic source 3 and a radiation detector 4, as indicated by the arrow A, is supported to allow rotation, so that fluoroscopy images can be recorded from different angles. A biplanar x-ray device can also be used as an alternative. A patient 6 is arranged on a bed 5. The ECG value of the patient is measured using suitable recording means 7, processed in an ECG control unit 8 and assigned to an ECG phase. The connection with the x-ray control unit 9 enables two fluoroscopy images at an angle to each other to be recorded using triggering in the same ECG phase with the aid of the x-ray system 2. A catheter 10 with an image recording device arranged at its tip, not shown in any greater detail here, is introduced into a hollow organ of the patient 6. The catheter control unit 11 monitors the catheter 10 and is also embodied to perform an even withdrawal of the catheter through the hollow organ while precisely recording the withdrawal length. In addition a possibly further control unit 12 is provided for the image recording device of the catheter 10. The control unit 12 has a communication connection to the ECG control unit 8, so that an ECG triggering or recording can be undertaken. All control units 8, 9, 11 and 12 also communicate with a central processing unit 13. A monitor 14 can be assigned to this unit, on which images, models and reconstructions can be displayed. The processing unit 13 is embodied in this case to execute the inventive method.

Figure 2:
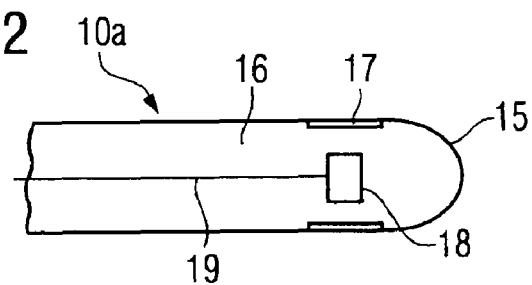
Figure 3:
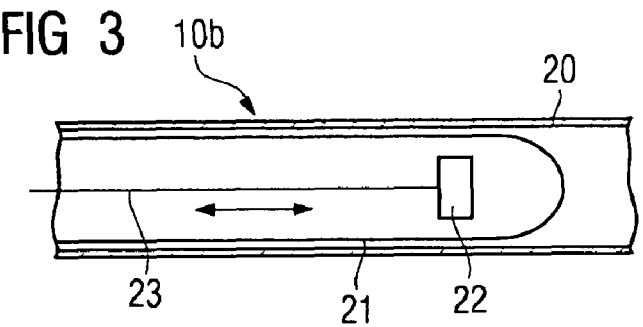

Within the framework of the present invention two types of catheter 10 can be used, these being shown in greater detail in FIGS. 2 and 3. FIG. 2 shows the catheter tip 15 of a first catheter 10a. An annular window 17 is provided which runs around the circumference of the catheter shell 16 in the area of the catheter tip 15, through which the images can be recorded with the aid of the image recording device 18. The image recording device 18 records two-dimensional sectional images of the hollow organ. It is connected via suitable signal lines 19, which run within the catheter shell 16, to the control unit 12 in which the images are detected and buffered.

A further catheter 10b is shown in FIG. 3. As a sleeve catheter it comprises an outer sleeve 12 which remains in position in the patient 6 during withdrawal, which is transparent is and serves as a catheter guide for the inner catheter 21, which in its turn comprises an image recording device 22 with assigned signal lines 23.

The image recording devices 18 or 22 recording sectional images of the hollow organ can be OCT, IVUS or OFDI devices in this case.

The diameter of the catheter 10 is smaller in this case than the diameter of the hollow organ, mostly even considerably smaller. Therefore the catheter 10 mostly does not align itself within the hollow organ 24, cf. FIG. 4, along a central path 25, but in the example shown follows a shortest path, even lying against the vessel wall 26 in some sections. In the example shown not even the start position 27 lies on the central path 25. If the catheter 10 is now withdrawn in the direction of the arrow B, its catheter tip 28 will not move along the central path 25, but will take another withdrawal path which essentially depends on the physical characteristics of the catheter 10 and of the hollow organ 24.

The effects of the behavior on the catheter images recorded are explained in greater detail by FIG. 5. This once more shows the hollow organ 24 and also its central path 25. A sectional image recorded at point 29 with an orientation of the catheter tip along the local direction of the central path 25 would represent a section through the plane 30 at right angles to the direction of the central path 25, with the catheter 10 lying precisely in the middle of the sectional image. Such a catheter image is shown at 48. The solid line represents the real withdrawal path 31 which the catheter 10 takes. In this case an image is recorded at point 32. The catheter tip of the catheter 10 is not located here in the center of the hollow organ 24 and is oriented along the direction of the real withdrawal path 31. This produces a slightly distorted catheter image 33, in which the catheter 10 is not arranged in the middle of the lumen. It should be pointed out here that the hollow organ is obviously generally not round and the orientation of the catheter can thus also not be determined with reference to the elliptic shape of the recorded lumen.

To reconstruct from the two-dimensional catheter images a 3D presentation of the hollow organ, to achieve the most correct possible presentation the orientation and the deviation of the position of the catheter tip from the central path must consequently be known for each of these catheter images.

FIG. 6 shows a flowchart of the method in accordance with the invention, as can be executed in the examination apparatus depicted in FIG. 1. At the start, step 34, the catheter 10 is moved to its start position in the hollow organ. However the catheter 10, since it was pushed in must not necessarily have followed the shortest path to the start position. So that this is adopted, in step 35 the catheter 10 is automatically advanced a slight distance distally by the catheter control unit 11, in order to be withdrawn into the start position thereafter. This stiffens the catheter 10 and it assumes approximately the shortest path. Then, in step 36, two two-dimensional fluoroscopy images are recorded at an angle to each other with the aid of the x-ray system 2. If the heartbeat, that is the phase of the heart cycle or the breathing cycle of the patient 6, effects the hollow organ to be examined, two options are conceivable. One is that only two images are recorded for the same ECG phase, triggered via the ECG control device 8. The catheter images are then triggered with the same ECG phase later during automatic withdrawal. It is however also possible to record two fluoroscopy images for each ECG phase of the heart cycle. The instantaneous ECG phase is then stored with the images. Since this also occurs later when the catheter images are recorded, the images of the same ECG phases can be assigned to each other. The same obviously applies to the breathing cycle of the patient 6, provided this is relevant.

The three-dimensional model is then created in step 37. In this case a sleeve catheter is not used as then starting point, but rather a normal catheter 10a. The lumen of the hollow organ can now be reconstructed from the two-dimensional fluoroscopy images, where necessary for each ECG phase. If previously recorded image data sets are available, from which, if necessary more exactly, a model of the hollow organ can be derived, for example magnetic resonance images or computer tomography images, then, as shown in 38, this image data can serve as a basis for creating the three-dimensional model. The fluoroscopy images recorded in step 36 are then used for registration of the two coordinate systems. Here too ECG or breathing phase should be noted where necessary.

In step 39 the three-dimensional start position of the catheter 10 is then determined in the three-dimensional model. If the three-dimensional model has been created from the fluoroscopy images recorded in step 36, in which the catheter tip is also to be seen, the position of the catheter tip can be determined directly in the three-dimensional model. Otherwise there must be reference back to the registration which links the coordinate systems. Then the catheter 10 is automatically withdrawn in step 40 by the catheter control unit 11 while recording the two-dimensional catheter images, here sectional images, and while detecting a withdrawal length automatically assigned to the catheter image. In addition the associated ECG phase for each catheter image can be determined via the ECG control unit 8 if necessary and stored assigned to this image. Alternatively it is possible for the catheter images to be recorded ECG-triggered.

Then, in step 41 the most probable withdrawal path of the catheter 10 from the start position is determined on the basis of the three-dimensional model. This is done with the aid of the processing unit 13 and a simulation which takes account both of the geometrical conditions of the lumen which are contained in the three-dimensional model and also physical principles as well as physical characteristics of the real or virtual catheter as well as of the hollow organ. The catheter's diameter, specific weight, elasticity, rigidity and/or surface properties can be used for example as physical parameters which describe the catheter. These parameters can be both measured characteristics of the real catheter 10 and also assumed characteristics of the virtual catheter. The characteristics of the hollow organ are taken into account by a model for hollow organ deformations which occur. In addition possible discontinuous movements of the catheter 10 are taken into account in the simulation. Examples of this are jumping across to another wall of the hollow organ or jumping further along the wall. After the most probable withdrawal path has been determined by the simulation by means of the processing unit 13, in step 42 the deviation of the position of the catheter 10 from a central path leading through the middle of the hollow organ and the orientation of the catheter 10 can be determined for each catheter image. This is possible using the detected and recorded withdrawal length. The withdrawal length of the real catheter 10 corresponds to a withdrawal length of the virtual catheter along of the most probable withdrawal path. Each catheter image is consequently assigned the deviation from the central path and the orientation to the corresponding position of the withdrawal path determined.

In step 43 the deviation from the central path is additionally determined from the catheter image. Now the difference between the deviation from the most probable withdrawal path determined and the deviation determined from the catheter image can be formed. This difference is compared in step 44 with a threshold value. If the difference is greater than the threshold value, the catheter 10 has evidently not followed the predicted withdrawal path but another path. In this case in step 45 the current position of the catheter 10 is set during image recording as the start position and the probable withdrawal path is determined once again in step 41 with this start position. If the difference is less than the threshold value in step 44, then, step 46, either the next catheter image is processed or, if this was the last catheter image, in step 47 the 3D presentation is reconstructed.

At this point a general remark is included about the sequence of the method steps. The three-dimensional model, the start position determined within it and the withdrawal path determined from it are only linked to each other in step 42. Steps 37, 39 and 41 must always be performed in the order shown. When however the withdrawal of the catheter 10 is performed precisely in step 40, it is not decisive for the success of the inventive method, provided this lies after step 36, the detection of two fluoroscopy images, and before step 42, in which the three-dimensional model and the detected catheter images are related to each other.

There can however be provision for the steps 42, 43 and 44 to be performed in parallel with step 40, that is directly after each recording of a catheter image. If a deviation from the withdrawal path is established, provided there is a difference exceeding the threshold value, is established in step 44, the withdrawal can be interrupted if necessary and new two-dimensional fluoroscopy images can be recorded, from which the new start position inclusive orientation can be determined exactly.

For the reconstruction of the 3D presentation in step 47, the ECG phases or breath phases can again be taken into account if necessary. Thus for each ECG phase a separate 3D presentation is determined if there has been no ECG triggering. The different 3D presentations can then either be fused into a single 3D presentation or appended to each other for forming a complete heart cycle as a film.

It is important however that in step 47 for the deviation from the central path and orientation assigned to each image in step 42 to be taken into account in the reconstruction, which means that the errors arising from this will be corrected as much as possible. This means that in the final analysis a more correct 3D presentation of the hollow organ is obtained.

Finally it remains to be pointed out that, for reconstruction of the 3D presentation, images derived from the catheter images, such as elastography images for example, can be used.

The invention claimed is:

1. Method for reconstructing a 3D presentation of a hollow organ of a patient based on a plurality of two two-dimensional catheter images detected by a withdrawn catheter including a recording device, comprising:
    recording at least two fluoroscopy images at two different angles showing the hollow organ and a tip of the catheter;
    determining a three-dimensional start position of the catheter from the fluoroscopy images in a three-dimensional model of the hollow organ;
    determining a most probable withdrawal path of the catheter based on the three-dimensional model of the hollow organ;
    withdrawing the catheter from the start position while recording the two-dimensional catheter images;
    assigning a withdrawal length to each two-dimensional catheter image;
    determining a deviation of a position of the catheter from a central path running through a middle of the hollow organ and an orientation of the catheter for each two-dimensional catheter image based on the most probable withdrawal path and the withdrawal length; and
    reconstructing the 3D presentation of the hollow organ based on the two-dimensional catheter images as well as the deviation of the position of the catheter from the central path and the orientation of the catheter,
    wherein the deviation of the position of the catheter from the central path is determined from the catheter images during the reconstruction,
    wherein a fixed threshold for a difference of the deviation from the central path determined from the most probable withdrawal path and from the catheter images is predetermined,
    wherein if the difference exceeds the fixed threshold, the most probable withdrawal path is recalculated from a position at which the threshold is exceeded, and
    wherein the recalculated most probable withdrawal path is used for reconstructing the 3D presentation of the hollow organ.

2. The method as claimed in claim 1,
    wherein the catheter is a sleeve catheter with a sleeve used as a catheter guide and the recording device of the catheter is withdrawn within the sleeve,
    wherein a three-dimensional model of the catheter guide is created based on fluoroscopy images of the sleeve or the catheter guided in the sleeve, and
    wherein the three-dimensional start position of the catheter is determined in the three-dimensional model of the catheter guide.

3. The method as claimed in claim 1, wherein the three-dimensional model of the hollow organ is created based on the fluoroscopy images.

4. The method as claimed in claim 1,
wherein the three-dimensional model of the hollow organ is created based on a previously recorded image data set of the hollow organ,
wherein the start position of the catheter is determined by registering the fluoroscopy images with the previously recorded image data set, and
wherein the previously recorded image data set is a magnetic resonance image data set or a computer tomography image data set.

5. The method as claimed in claim 1, wherein the most probable withdrawal path is determined by:
positioning a virtual catheter at the start position in the three-dimensional model of the hollow organ, and
simulating the virtual catheter in the three-dimensional model.

6. The method as claimed in claim 5, wherein a parameter of the simulation is a physical parameter of the catheter.

7. The method as claimed in claim 6, wherein the physical parameter of the catheter is selected from the group consisting of: diameter, weight, elasticity, rigidity, and surface property.

8. The method as claimed in claim 5, wherein the three-dimensional model of the hollow organ comprises a model for a deformation of the hollow organ.

9. The method as claimed in claim 5,
wherein the simulation simulates a possible discontinuous movement of the catheter, and
wherein the discontinuous movement of the catheter is a jump from a wall of the hollow organ across to another wall of the hollow organ or a jump forward along the wall of the hollow organ.

10. The method as claimed in claim 1, wherein the recording of the fluoroscopy images and the catheter images are triggered by a fixed ECG phase of the patient and the ECG phase is identical for both the fluoroscopy images and the catheter images.

11. The method as claimed in claim 1, wherein the catheter images are recorded at different ECG phases and the hollow organ is reconstructed for each ECG phase from catheter images having the same ECG phase.

12. The method as claimed in claim 11,
wherein the fluoroscopy images are recorded over at least one entire heart phase, and
wherein at least two of the fluoroscopy images are assigned to the catheter images having an identical ECG phase with the two fluoroscopy images for the 3D reconstruction.

13. The method as claimed in claim 12, wherein the 3D reconstruction is fused together for various ECG phases.

14. The method as claimed in claim 12, wherein the 3D reconstruction is combined into a 4D reconstruction for each ECG phase.

15. The method as claimed in claim 1, wherein the catheter is first pushed a short distance beyond the start position and then is pulled back to the start position.

16. The method as claimed in claim 1, wherein the recording device of the catheter is selected from the group consisting of: an IVUS, an OCT, and an OFDI.

17. A medical system for reconstructing a 3D presentation of a hollow organ of a patient, comprising:
a catheter that records a plurality of two-dimensional catheter images of the hollow organ while withdrawing the catheter from a start position in the hollow organ;
a catheter control unit that assigns a withdrawal length to each two-dimensional catheter image;
an x-ray device that records at least two fluoroscopy images at two different angles showing the hollow organ and a tip of the catheter; and
a processing unit that:
determines the start position of the catheter from the fluoroscopy images in a three-dimensional model of the hollow organ,
determines a most probable withdrawal path of the catheter based on the three-dimensional model of the hollow organ,
determines a deviation of a position of the catheter from a central path running through a middle of the hollow organ and an orientation of the catheter for each two-dimensional catheter image based on the most probable withdrawal path and the withdrawal length, and
reconstructs the 3D presentation of the hollow organ based on the two-dimensional catheter images as well as the deviation of the position of the catheter from the central path and the orientation of the catheter,
wherein the deviation of the position of the catheter from the central path is determined from the catheter images during the reconstruction,
wherein a fixed threshold for a difference of the deviation from the central path determined from the most probable withdrawal path and from the catheter images is predetermined,
wherein if the difference exceeds the fixed threshold, the most probable withdrawal path is recalculated from a position at which the threshold is exceeded, and
wherein the recalculated most probable withdrawal path is used for reconstructing the 3D presentation of the hollow organ.

18. The medical system as claimed in claim 17,
wherein the catheter is a sleeve catheter with a sleeve used as a catheter guide and a recording device of the catheter is withdrawn within the sleeve,
wherein a three-dimensional model of the catheter guide is created based on fluoroscopy images of the sleeve or the catheter guided in the sleeve, and
wherein the three-dimensional start position of the catheter is determined in the three-dimensional model of the catheter guide.

* * * * *